United States Patent [19]
Maltby

[11] 3,936,738
[45] Feb. 3, 1976

[54] METHOD OF AND APPARATUS FOR MEASURING THE AMOUNT OF COATING MATERIAL APPLIED TO SUBSTRATES

[75] Inventor: Frederick L. Maltby, Jenkintown, Pa.

[73] Assignee: Drexelbrook Controls, Inc., Glenside, Pa.

[22] Filed: Jan. 2, 1974

[21] Appl. No.: 429,743

[52] U.S. Cl............ 324/71 R; 324/65 R; 324/30 R
[51] Int. Cl.² .................. G01N 27/00; G01R 27/02
[58] Field of Search......... 324/71 R, 65 R, 61, 30 R

[56] References Cited
UNITED STATES PATENTS

| | | | |
|---|---|---|---|
| 2,008,046 | 7/1935 | Snelling | 324/65 |
| 3,043,993 | 7/1962 | Maltby | 324/61 X |
| 3,358,223 | 12/1967 | Birnstingl | 324/65 X |
| 3,746,975 | 7/1973 | Maltby | 324/65 |

Primary Examiner—Alfred E. Smith
Assistant Examiner—Rolf Hille
Attorney, Agent, or Firm—Woodcock, Washburn, Kurtz & Mackiewicz

[57] ABSTRACT

The conductivity and temperature of a coating material before application to a substrate are measured. The overall conductance and the elevated temperature of the coating material after application to the substrate are also measured. A temperature corrected conductivity is then determined from the measured conductivity and the temperature differential between the coating material before and after application to the substrate. Measured overall conductance is then divided by the corrected conductivity to determine the thickness. In addition, the dry weight of the coating may be determined by multiplying the thickness times the density of the coating material times the fractional solids weight.

9 Claims, 6 Drawing Figures

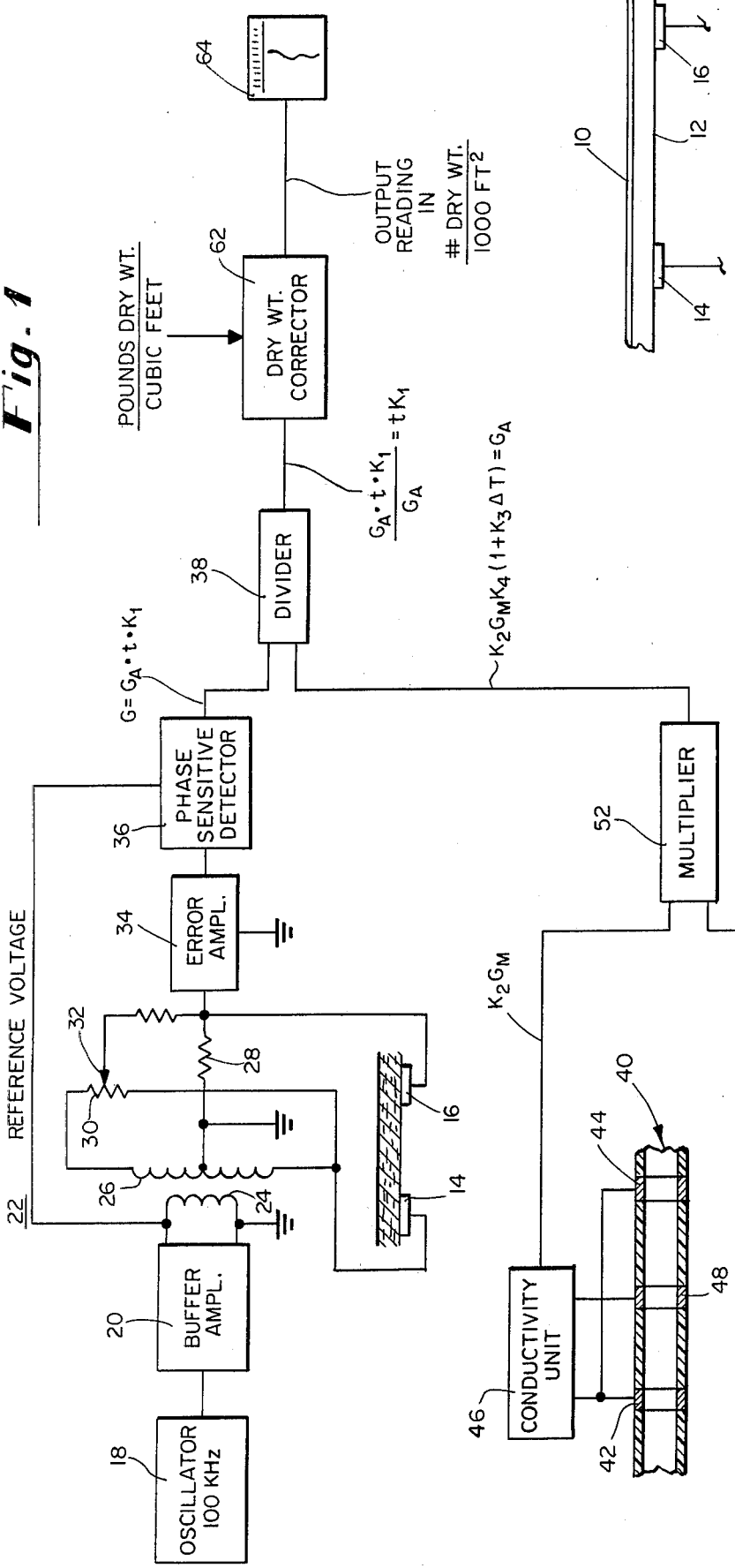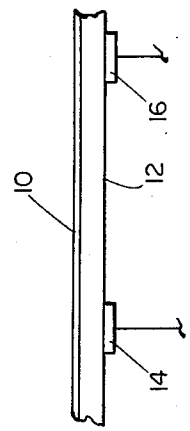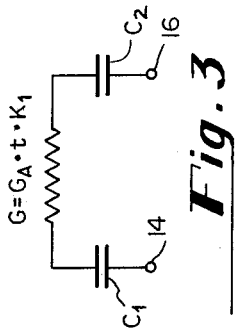

ND OF APPARATUS FOR MEASURING
THE AMOUNT OF COATING MATERIAL APPLIED
TO SUBSTRATES

BACKGROUND OF THE INVENTION

This invention relates to the application of coatings to substrates and measurements of the thickness and/or the dry weight of the coatings on the substrates. This invention also relates to controlling the application of coating materials to substrates.

This invention is particularly useful for measuring wet clay coatings which are applied to paper or pasteboard or box-board substrates to provide a smooth white printable surface on the substrates. In order to properly control the application of clay coatings to the paste-board substrate, it is desirable to obtain some sort of measurement on the coating material which has been applied to previously coated substrates so as to correct for any undesirable deviations on subsequently coated substrates. More particularly, it is desirable to obtain thickness and/or dry weight measurements of the coatings on substrates so as to properly control the application of coatings to other substrates.

Prior art nuclear absorption techniques for performing these measurements on coatings are not well adapted for use in this application since these techniques will not distinguish between a variation in the thickness of the substrate and a variation in the thickness of the coating material. Since the coating may only be a few thousandths of an inch thick, and the pasteboard substrate may be as much or more than forty times thicker than the coating, any slight variation in the paste-board substrate will result in very serious errors in the measurement of the coating thickness if the prior art nuclear techniques are utilized.

It has been recognized that the thickness of a relatively conductive film on an insulating substrate may be measured by determining the conductance of the coated substrate since fluctuations in the thickness of the substrate will have little or no effect on the measured conductivity. Such an arrangement is shown in U.S. Pat. No. 3,043,993 wherein the amount of glue on paper is measured utilizing two plate electrodes in contact with the side of the paper opposite the side on which the glue is applied. However, the actual conductance which is measured varies as a function of temperature and can lead to erroneous indications that the amount of glue has varied when in fact only the temperature has varied.

U.S. Pat. No. 3,491,595 - Griffeth discloses a system for measuring the conductivity of soil to determine the moisture content of the soil utilizing a temperature sensing element to compensate for variations in temperatures sensed by a soil probe. If such compensation were utilized with the system described in my U.S. Pat. No. 3,043,993, the system would provide an indication of the overall conductance of the conductive coating but would not provide an indication of the thickness of the coating.

SUMMARY OF THE INVENTION

It is an overall object of this invention to provide a method and apparatus for determining the thickness of a coating on a substrate regardless of temperature changes in the coating material.

In a preferred embodiment of the invention, apparatus is provided comprising conductivity measuring means for generating a signal representing the conductivity of the coating material at a reference temperature before application of the coating material to the substrate. Temperature measuring means generate a signal representing the difference in temperature of the coating material before application to the substrate and the temperature of the coating after application to the substrate. Conductance measuring means generate a signal representing the overall conductance of the coating material on the substrate at the actual temperature of the coated substrate. A first circuit means coupled to the conductivity measuring means and the temperature measuring means generate a conductivity correction signal representing the conductivity of the coating material at the temperature of the coated substrate in response to the temperature difference signal and the conductivity signal. A second circuit means is coupled to the first circuit means and the conductance measuring means for generating a signal representing the thickness of the coating material in response to the conductance signal and the conductivity correction signal.

In accordance with one important aspect of the invention, the temperature sensing means comprises a first temperature sensing element in thermal communication with the coating material at the conductivity measuring means and a second temperature sensing element in thermal communication with the coating on the substrate.

In accordance with another important aspect of the invention, conductivity measuring means comprises a conductivity circuit means having a pair of input terminals and means for establishing a flow path of the coating material where the input port and the output port of the flow path are electrically connected to one of the input terminals and an intermediate point along the flow path insulated from the input port and the output port is electrically connected to other of the input terminals. In the preferred embodiment of the invention, the flow path comprises a first conductive block means having a pair of passageways forming the input port and the output port of the flow path and a second conductive block forming a flow path therethrough with one end of the flow path connected to the input port by a first insulated conduit and the other end of the flow path through the second conductive block connected to the output port of the first conductive block by a second insulated conduit.

In accordance with another important aspect of the invention, the apparatus comprises means for applying the coating material to the substrate and means for drying the material on the substrate at an elevated temperature. Means are coupled to the second circuit means for controlling the application of the coating material to the substrate in response to the signal representing the thickness of the coating material.

BRIEF DESCRIPTION OF THE DRAWINGS

FIG. 1 is a schematic diagram of a circuit embodying the invention;

FIG. 2 is an enlarged sectional view of the measuring electrodes of the circuit shown in FIG. 1 in contact with a coated substrate;

FIG. 3 is the equivalent circuit of the coated substrate shown in FIG. 2 as it appears at the measuring electrodes;

DETAILED DESCRIPTION OF A PREFERRED EMBODIMENT

Figure 4:
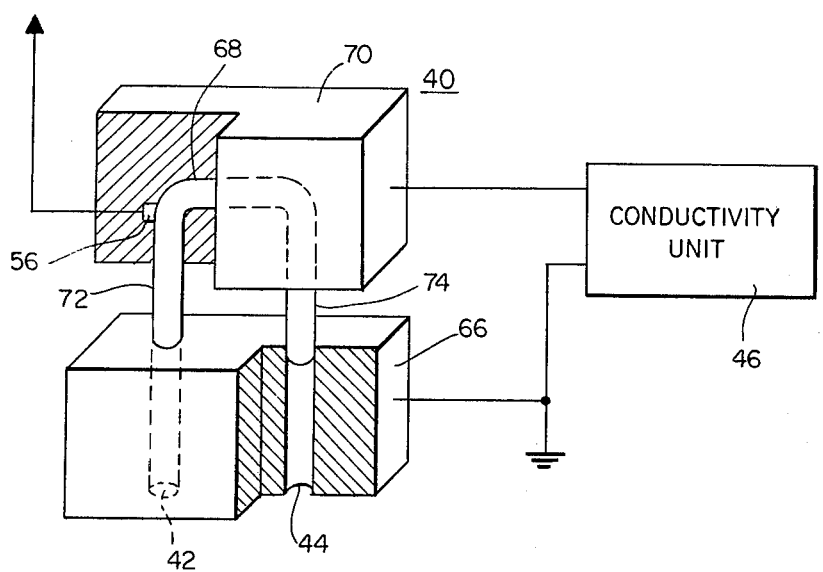
FIG. 4 is an enlarged partially sectioned view of the conductivity measuring apparatus which is shown in schematic form in FIG. 1.

In accordance with this invention, the thickness of a wet conductive coating 10 applied to an insulating substrate 12 as shown in FIG. 2 is determined by measuring the impedance or admittance between a pair of flat or planar electrodes 14 and 16 which are in close proximity or contact with the surface of the substrate 12 opposite the surface on which the coating 10 is applied. An equivalent circuit of the impedance or admittance between the electrodes 14 and 16 is shown in FIG. 3 wherein a capacitor $C_1$ represents the capacitive coupling through the substrate 12 between the coating 10 and the electrode 14 while a capacitor $C_2$ represents the capacitive coupling through the substrate 12 from the electrode 16 to the coating 10. The conductance of the coating 10 is represented by a resistor having a conductance $G = G_a \cdot t \cdot K_1$ where $G_a$ is the conductivity of the coating material, t is the thickness of the coating material and $K_1$ is a proportionality constant which is a function of the measuring geometry and particularly dependent upon the distance between the two electrodes 14 and 16. It will therefore be seen that a change in the overall conductance of the coating 10 as seen by the electrodes 14 and 16 will reflect a change in thickness and/or a change in the conductivity of the coating material which might result from a change in temperature.

In order to confine the measurement made between the electrodes 14 and 16 to the overall conductance G, it is necessary to eliminate the capacitive coupling through the substrate 12 as represented by the capacitors $C_1$ and $C_2$ of FIG. 3. In this connection, the area of the electrodes 14 and 16 are made large and then only the conductive portion of the admittance between the electrodes 14 and 16 is measured. As long as the reactance of the capacitors $C_1$ and $C_2$ is much smaller than the resistance through the coating (the reciprocal of conductance), the conductance measured between the electrodes 14 and 16 will be essentially equal to the conductance G of the coating itself.

A circuit for converting the measurement of the conductance G into a measurement of the thickness t independent of the temperature of the coated substrate will now be described in detail with reference to the schematic circuit diagram of FIG. 1. The measurement of the conductance G between the electrodes 14 and 16 is made utilizing circuitry comprising an oscillator 18 which may generate a frequency of the order of 100 KHz., a buffer amplifier 20 coupled to the output of the oscillator 18 and a bridge transformer 22 having a primary 24 connected across the output of the buffer amplifier 20 and secondary 26.

One-half of the bridge output is applied across electrodes 14 and 16 in series with a small load resistor 28 which is sufficiently small so that the current flowing through the resistor 28 is determined only by the impedance between the electrodes 14 and 16. A resistor 30 is connected across the secondary 26 with a movable tap 32 which may be adjusted to pass a trimming current into the resistor 28 where the trimming current is of a phase and magnitude as required to balance any undesired currents which may flow between the electrodes 14 and 16.

The voltage across the resistor 28, which is proportional to the admittance between the electrodes 14 and 16 is applied to the input of an error amplifier 34 which is designed for stable gain with no phase shift. The output of the error amplifier 34 is applied to a phase sensitive detector 36 phased to rectify only the in-phase component of the voltage, i.e., that phase which is produced from the conductance between the electrodes 14 and 16. The output of the detector 36 is a DC voltage directly proportional to the conductance between the electrodes and also directly proportional to the product of actual conductivity of the coating material times the coating thickness t times the proportionality constant $K_1$.

The overall conductance signal G is then applied to a divider circuit 38. In order to generate a signal repretenting the thickness t and independent of any variation in the conductivity $G_a$ due to changes in temperature it is necessary to divide the signal G by a conductivity correction signal $G_a$ which is generated in the following manner.

The coating material prior to application to the substrate 12 moves along a flow path through a conductivity cell 40 having a conductive input port electrode 42 and a conductive output port electrode 44 which are electrically connected to a ground terminal of a conductivity measuring unit 46 such as the Drexelbrook Engineering model 408-4000 modified for conductance measurements utilizing a 100 KHz. setting. A conductive member 48, located at an intermediate point between the conductive input ports 42 and 44, is electrically connected to another terminal of the conductivity unit 46. Those portions of the flow path between the conductive input ports 42 and 44 and the conductive member 48 are formed by insulating conduits.

The output of the conductivity unit 46 is a signal representing $K_2G_m$ where $G_m$ is the conductivity of the coating material in the conductivity cell and $K_2$ is a proportionality constant. The signal $K_2G_m$ is then applied to a multiplier 52. The other signal applied to the multiplier 52 is generated by circuitry including a thermocouple 54 which is in substantially direct thermal communication with the coating 10 applied to the substrate 12 and a thermocouple 56 which is in substantially direct thermal communication with the coating material flowing through the flow path of the conductivity cell. The outputs from the thermocouples 54 and 56 are applied to a differential amplifier to generate a signal representing $K_3(t_a-t_m)$ or $K_3\Delta t$ where $K_3$ is a porportionality constant. The signal $K_3\Delta t$ is applied to a summer 60 along with a 1 volt signal to generate a signal representing $K_4(1+K_3\Delta t)$ where $K_4$ is another proportionality constant and this signal is multiplied by the signal $K_2 G_m$ at the multiplier 52 to generate a signal $K_2G_mK_4(1+K_3\Delta t) = G_a$.

By dividing the signal G by $G_a$ at the divider 38, a signal $tK_1$ is obtained which represents the thickness of the coating material times the proportionality constant $K_1$ independent of the actual conductivity of the coating material.

The output of the divider 38 which is directly proportional to the thickness of the coating 10 is applied to the input of a dry weight corrector 62. In this unit, the signal is multiplied by a quantity which is proportional to the dry weight per cubic foot of coating material, and the output of the unit 62 is directly proportional to the dry weight of the coating per unit area. By applying the signal from the output of the dry weight corrector unit 62 to a suitable indicator or recorder 64, the dry weight of the coating per unit area may be displayed in an appropriate unit such as pounds per thousand square feet.

As shown in FIG. 1, the conductivity cell 40 is shown as a linear flow path between the input port electrode 42 and the output port electrode 44. Actually, and in accordance with one important aspect of the invention, the flow path through the conductivity cell 40 is U-shaped as shown in FIG. 4 where the input port 42 and the output port 44 are formed by a first conductive block 66 which is directly connected to the grounded terminal of the conductivity measuring unit 46. The input port 42 and the output port 44 are connected to a U-shaped flow path 68 in a second conductive block 70 through insulating conduits 72 and 74. The conductive block 70 is then connected to the other terminal of the conductivity unit 46. The thermocouple 56 is embedded within the block 70 to provide a signal representing temperature of the coating material as the material flows through the conductive block 70.

Figure 4A:
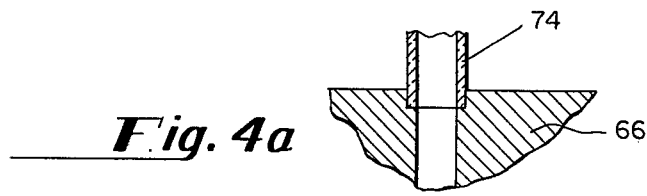
FIG. 4a is a fragmentary enlarged view of the section shown in FIG. 4.

As best shown in FIG. 4a, the insulating tubes 72 and 74, which may comprise glass extending into blocks 66 and 68, which may comprise any suitable conductor such as carbon or a metal. By operating the conductivity unit at an RF frequency such as 100 KHz., the interface losses between the conductive blocks and the solution passing through the conductive blocks is minimized without platinizing the walls along the flow paths through the conductive blocks.

By utilizing the arrangement shown in FIG. 4, both ends of the flow path through the conductivity cell 40 as represented by ports 42 and 44 are maintained at ground potential so that the conductivity measurement is made in both directions through the flow path. If only one end of the flow path through the cell 40 were grounded, errors in the conductivity measurement could occur due to changes in the conductivity through the cell toward the other end of the flow path.

Figure 5:
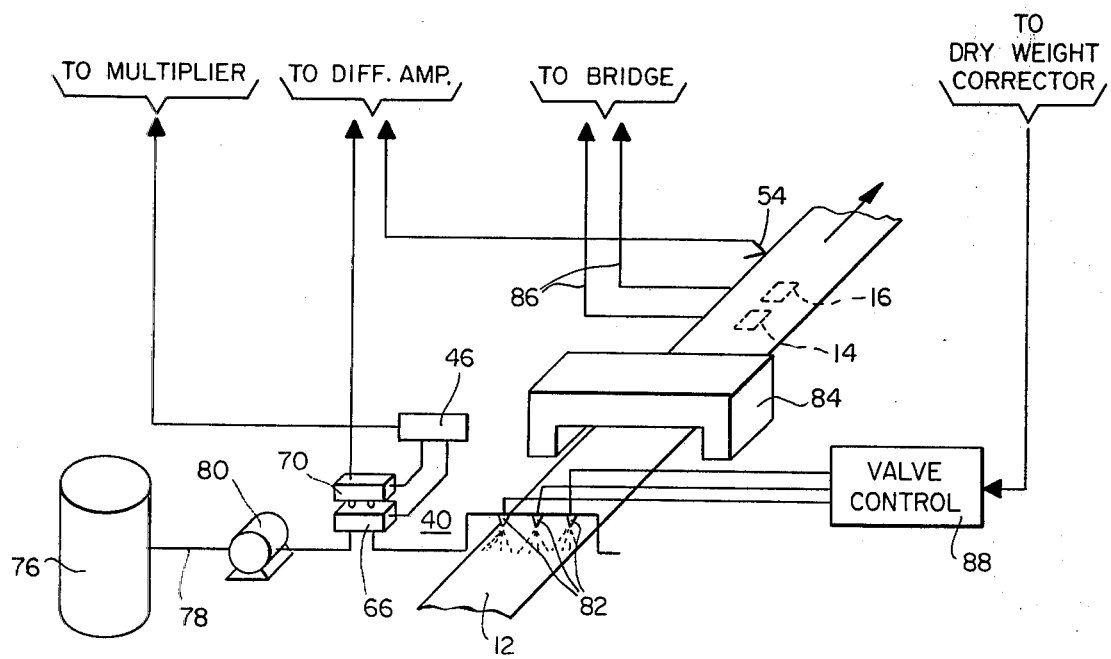
FIG. 5 is a pictorial representation of a system for controlling the thickness of the coating applied to a substrate.

FIG. 5 depicts a system for the controlled application of a coating material to a substrate utilizing this invention. As shown in FIG. 5, the coating application system comprises a tank 76 for storing the coating material prior to its application to a substrate 12. The coating material from the tank 76 is moved through a line 78 by a pump 80 where the line 78 is in series with the conductivity cell 40 and a plurality of nozzles 82 which direct the coating material to the substrate 12. After the substrate has been coated with the material flowing from the nozzle 82, it passes through a dryer 84 which heats the coated substrate to an elevated temperature. After the substrate moves from the dryer 84 it is conveyed in the direction shown by the arrow. The uncoated surface of the substrate passes over the conductivity measuring electrodes 14 and 16 (shown in dotted outline) which are connected into the bridge circuit at the input to the error amplifier 34 through lines 86. The thermocouple 54 is maintained in close thermal communication with the dried substrate. In accordance with this invention, the signal from the dry weight corrector 62 is applied to a valve control 88 to open and close the valves in the nozzles 82 in a manner so as to control the thickness of the coating applied to the substrate 12.

Although the means for generating the signal representing the pounds dry weight per cubic foot of coating material which is applied to the dry weight corrector 62 has not been shown, it will be understood that this signal may be generated in a number of ways. One of these ways involves double multiplication. A first factor of total weight per cubic foot (density) is multiplied by the dry weight pounds per pound of coating material (fractional solids weight). Another way involves multiplication of a quantity which is the density of the coating material minus the density of water with the whole quantity being multiplied by a constant which depends upon the average density of the dry solids.

In the embodiment previously shown as described, the conductance of the coating is measured without interference from the capacitance of the substrate by utilizing relatively large electrodes 14 and 16, e.g., 5 to 25 square inches in area each so as to assure that the coupling impedance is less than 10 percent of the resistance. The conductance may also be measured by measuring both the real and imaginary parts of the admittance between the electrodes 1 and 2 as set forth in my U.S. Pat. No. 3,746,975 assigned to the assignee of this invention.

As shown in FIG. 5, the electrodes 14 and 16 in effect scan the substrate 12 as the substrate 12 moves over the electrodes 14 and 16 after leaving the dryer 84. It will of course be appreciated that the electrodes may scan the substrate 12 transversely so as to provide a uniform cross-sheet profile. It is also possible to selectively control the nozzles 82 with respect to one another in response to the transverse scanning so as to maintain a uniform cross-sheet profile. Further, it is possible to utilize an air knife so as to blow excess coating off the substrate in response to the sensing of a nonuniformity in thickness.

As utilized herein, a signal "representing" a physical measurement does not necessarily means that a characteristic of the signal, e.g., amplitude or phase, is proportional to the physical measurement. Rather, the term "representing" merely means that the signal carries information fully descriptive of the physical measurement and this information is readily derived from the signal if the signal is suitably operated upon.

Although a specific embodiment of the invention has been shown and described and particular modifications have been suggested, it will be understood that all embodiments in my application which would occur to those of ordinary skill in the art fall within the true spirit and scope of the invention as set forth in the appended claims.

What is claimed is:

1. Apparatus for determining the thickness of a coating on a substrate comprising:
   conductivity measuring means for generating a signal representing the conductivity of the coating material at a temperature before application to the substrate;
   temperature sensing means for generating a signal representing the difference in the temperature of said coating material before application to said substrate and the temperature of the coating on the substrate;
   conductance measuring means for generating a signal representing the overall conductance of the coating material on the substrate at the actual temperature of the coating material on the substrate; and circuit means coupled to said conductivity measuring means, said temperature sensing means and said conductance measuring means for generating a signal representing the thickness of the coating material in response to said conductivity signal, said temperature difference signal and said conductance signal.

2. The apparatus of claim 1 wherein said circuit means comprises:

first circuit means coupled to said conductivity measuring means and said temperature sensing means for generating a conductivity correction signal representing the conductivity of the coating material at the temperature of the coated substrate in response to the temperature difference signal and the conductivity signal; and second circuit means coupled to said first circuit means and said conductance measuring means for generating a signal representing the thickness of the coating material in response to said conductance signal and said conductivity correction signal.

3. The apparatus of claim 2 wherein said first circuit means comprises:

means for generating a constant signal;

summing means coupled to said temperature measuring means and said constant signal means for generating a sum signal representing the sum of said temperature difference signal and said constant signal; and multiplying means coupled to said summing means and said conductivity means for generating a product signal representing the product of said sum signal and said conductivity signal.

4. The apparatus of claim 3 wherein said second circuit means comprises dividing means coupled to said conductance measuring means and said multiplying means for generating a signal representing said conductance signal divided by said product signals so as to represent the thickness of the coating material on said substrate.

5. The apparatus of claim 2 comprising third circuit means coupled to said second circuit means for generating a signal representing the dry weight of the coating material for a given area of the substrate.

6. The apparatus of claim 1 wherein said temperature sensing means comprises a first temperature sensing element in thermal communication with said coating material at said conductivity measuring means and a second temperature sensing element in thermal communication with said coating on said substrate.

7. The apparatus of claim 1 wherein said conductance measuring means comprises a pair of electrodes having substantially planar conductive surfaces extending parallel to said substrate.

8. The apparatus of claim 1 wherein said conductivity measuring means comprises a conductivity circuit means having a pair of input terminals and means for establishing a flow path of said coating material, the ends of said flow path being connected to one of said input terminals and an intermediate point of said flow path being connected to another of said input terminals.

9. The apparatus of claim 8 wherein said flow path means comprises a first conductive block means forming an input port and an output port, a second conductive block means having a path therethrough, a first insulated conduit extending between said input port of said first block and one end of the path through said second block and a second insulated conduit extending between the other end of said path through said second block and said output port of said first block so as to form a path of conductive material from said input port to said output port of said first block.

* * * * *